US012624359B2

(12) United States Patent
Kwok et al.

(10) Patent No.: US 12,624,359 B2
(45) Date of Patent: May 12, 2026

(54) L-RNA APTAMERS AND METHODS OF IDENTIFYING THE SAME

(71) Applicant: CITY UNIVERSITY OF HONG KONG, Kowloon (HK)

(72) Inventors: Chun Kit Kwok, Kowloon (HK); Danyang Ji, Kowloon (HK)

(73) Assignee: CITY UNIVERSITY OF HONG KONG, Kowloon (HK)

( * ) Notice: Subject to any disclaimer, the term of this patent is extended or adjusted under 35 U.S.C. 154(b) by 745 days.

(21) Appl. No.: 18/052,811

(22) Filed: Nov. 4, 2022

(65) Prior Publication Data

US 2023/0203503 A1 Jun. 29, 2023

Related U.S. Application Data

(60) Provisional application No. 63/394,847, filed on Aug. 3, 2022, provisional application No. 63/281,503, filed on Nov. 19, 2021.

(51) Int. Cl.
*C12N 15/115* (2010.01)
(52) U.S. Cl.
CPC ........ *C12N 15/115* (2013.01); *C12N 2310/16* (2013.01)
(58) Field of Classification Search
None
See application file for complete search history.

(56) References Cited

U.S. PATENT DOCUMENTS

2003/0127396 A1* 7/2003 Siddiqi ................. B03C 1/0335
210/695
2021/0171950 A1* 6/2021 Kwok ................ C12N 15/1048

OTHER PUBLICATIONS

Chan et al. Specific Binding of a D-RNA G-Quadruplex Structure with an L-RNA Aptamer. Angew. Chem. Int. Ed. 59:5293-5297 (2020). (Year: 2020).*
Chan Supporting Information [online] Feb. 12, 2020 [retrieved on Aug. 9, 2025] retrieved from https://onlinelibrary.wiley.com/doi/full/10.1002/anie.201914955 (Year: 2020).*

* cited by examiner

*Primary Examiner* — Samuel C Woolwine
(74) *Attorney, Agent, or Firm* — Conley Rose, P.C.; Michael W. Piper; Gayatry S. Nair

(57) ABSTRACT

Disclosed herein is a method of identifying an L-RNA aptamer specific for a target nucleic acid. According to some embodiments of the present disclosure, the method comprises, in vitro transcribing the DNAs of the DNA library into D-RNAs, followed by identifying target-specific D-RNAs via negative and positive selections, and then producing the L-RNA aptamer based on the identified D-RNA. Also disclosed herein are two aptamers identified by the present method. According to some embodiments of the present disclosure, the two aptamers respectively comprise the nucleotide sequences of SEQ ID NOs: 1 and 2.

3 Claims, 6 Drawing Sheets

Specification includes a Sequence Listing.

(SEQ ID NO: 1)

(SEQ ID NO: 2)

wild-type or mutant
*APP* sequence wild-type or mutant
*c-kit* sequence (A)

(B)

(C)

(D)

L-RNA APTAMERS AND METHODS OF IDENTIFYING THE SAME

CROSS-REFERENCE TO RELATED APPLICATIONS

This application relates to and claims the benefits of U.S. Provisional Application No. 63/281,503 filed Nov. 19, 2021, and U.S. Provisional Application No. 63/394,847 filed Aug. 3, 2022: the contents of these applications are incorporated herein by reference in their entirety.

INCORPORATION BY REFERENCE OF MATERIAL IN ASCII TEXT FILE

This application incorporates by reference the Sequence Listing in the following XML file being submitted concurrently with:

File name: HP0228US_US_seqlisting; created on Nov. 2, 2022; and having a size of 4.47 KB.

The information in the Sequence Listing is incorporated herein in its entirety for all purposes.

BACKGROUND OF THE INVENTION

1. Field of the Invention

The present disclosure in general relates to the field of L-form ribonucleic acid (L-RNA) aptamers. More particularly, the present disclosure relates to a method for identifying L-RNA aptamers, which recognize and bind to target nucleic acids having G-quadruplex (G4) structures.

2. Description of Related Art

Guanine (G)-rich sequences of single-stranded DNA and RNA can fold into stable, intra- or intermolecular secondary structures called G-quadruplexes (dG4s and rG4s). Four guanines interact with each other by Hoogsteen-hydrogen bonds to form a planar structure, G-quartet. Stacking of two or more G-quartets, connected by loop nucleotides forms a G4 structure, and it is further stabilized by monovalent cations ($K^+>Na^+>Li^+$). Over the years, rG4s have been reported to have key roles in gene regulation and cellular processes, such as transcription, RNA splicing, translation, RNA stability, RNA localization and others. In addition, new studies have associated rG4s with diseases and cancers, making them one of the promising therapeutic targets for drug development.

G4 targeting is a topic of emerging interest, and since the first report of G4-specific chemical in 1997, more than hundreds of G4 ligands have been developed. Currently, major approaches employed for G4 targeting include the development of G4-specific chemicals, peptides and antibodies. The generation and application of these G4 tools have greatly promoted the understanding of G4 structure and biology, and the elucidation of the three-dimensional (3D) high resolution structure of the binding complexes provided fundamental insights on the future enhancement of these G4 tools. Despite the significant progresses made, the selective targeting of G4 of interest is still challenging due to the structural similarity of G4s, with only limited success so far.

In view of the foregoing, there is a continuing interest in developing a novel method for developing G4-targeting tools.

SUMMARY

The following presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later.

As embodied and broadly described herein, one aspect of the disclosure is directed to a method of identifying an L-RNA aptamer specific for a target nucleic acid structure. The selection process starts from a deoxyribonucleic acid (DNA) library, in which the DNA library comprises a first plurality of DNAs respectively having randomized sequences. According to the embodiments of the present disclosure, the method comprises, (a) producing a first plurality of D-form RNAs (D-RNAs) respectively corresponding to the first plurality of DNAs via in vitro transcription;

(b) mixing the first plurality of D-RNAs of step (a) with a first plurality of streptavidin-coated magnetic beads, which are pre-treated with transfer RNAs (tRNAs);

(c) collecting and mixing the supernatant of the product of step (b) with a biotinylated target nucleic acid;

(d) mixing the product of step (c) with a second plurality of streptavidin-coated magnetic beads, which are pre-treated with the tRNAs;

(e) eluting the precipitate of step (d) with an elution buffer so as to produce a second plurality of D-RNAs that can bind to the target nucleic acid;

(f) producing a plurality of complementary DNAS (cD-NAs) respectively corresponding to the second plurality of D-RNAs of step (e) via reverse transcription;

(g) producing a second plurality of DNAs respectively corresponding to the plurality of cDNAs of step (f) via polymerase chain reaction (PCR);

(h) repeating steps (a) to (g) at least 4 times, in which the in vitro transcription was performed by using the product of step (g), so as to identify a D-RNA aptamer specific for the target nucleic acid; and (i) producing the L-RNA aptamer corresponding to the D-RNA aptamer of step (h).

In general, the target nucleic acid may be DNA or RNA. According to some embodiments of the present disclosure, the target nucleic acid has a G4 structure.

According to some exemplary embodiments, in the step (c), the biotinylated target nucleic acid is a biotinylated L-form RNA or DNA.

Optionally, the present method further comprises (b-1) subjecting the product of step (b) to centrifugation or magnetic field prior to step (c).

Still optionally, the present method further comprises (d-1) subjecting the product of step (d) to centrifugation or magnetic field prior to step (e).

Also disclosed herein are two L-RNA aptamers identified by the present method. According to the embodiments of the present disclosure, the L-RNA aptamers are respectively designated as "L-Apt.8f" and "L-Apt.12-6".

According to some embodiments, the L-RNA aptamer L-Apt.8f exhibits binding specificity for the 3'-untranslated region (3'-UTR) of amyloid precursor protein (APP) messenger RNA (mRNA), and comprises the nucleotide sequence of SEQ ID NO: 1.

According to certain embodiments, the L-RNA aptamer L-Apt.12-6 exhibits binding specificity for a target nucleic acid having a parallel G4 structure (for example, c-kit 1 dG4 in the promoter of c-KIT gene), and comprises the nucleotide sequence of SEQ ID NO: 2.

Many of the attendant features and advantages of the present disclosure will becomes better understood with reference to the following detailed description considered in connection with the accompanying drawings.

BRIEF DESCRIPTION OF THE DRAWINGS

The present description will be better understood from the following detailed description read in light of the accompanying drawings, where:

FIG. 2A: Plasmid containing wild-type or mutant APP sequence, in which the wild-type or mutant APP sequence was inserted into the 3'-UTR of the *Renilla* luciferase gene: FIG. 2B: Plasmid containing wild-type or mutant c-kit sequence, in which the wild-type or mutant c-kit sequence was inserted into the HSV-TK promoter:

Figure 1A:
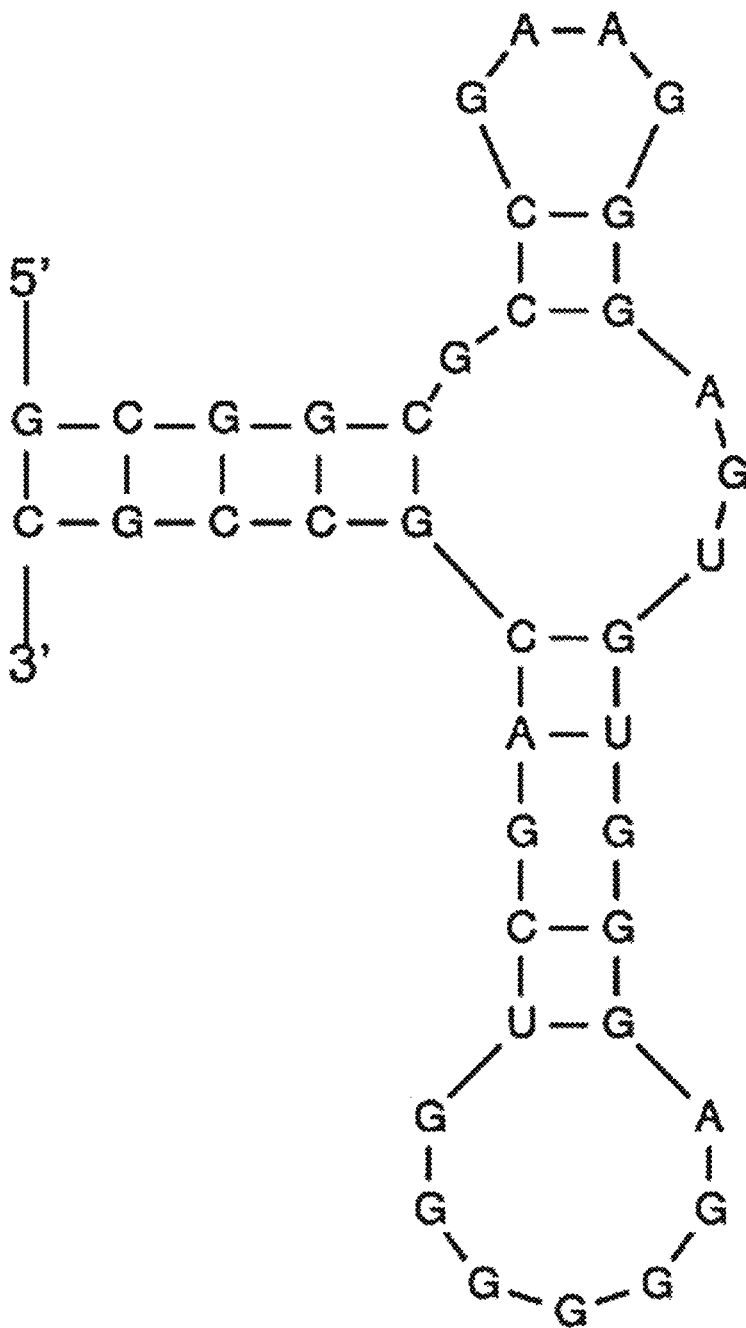
FIGS. 1A and 1B are schematic diagrams respectively depicting the predicted secondary structures of aptamers L-Apt.8f (SEQ ID NO: 1) (FIG. 1A) and L-Apt.12-6 (SEQ ID NO: 2) (FIG. 1B) according to one embodiment of the present disclosure.

In accordance with common practice, the various described features/elements are not drawn to scale but instead are drawn to best illustrate specific features/elements relevant to the present invention.

DETAILED DESCRIPTION OF THE INVENTION

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

I. DEFINITION

For convenience, certain terms employed in the specification, examples and appended claims are collected here. Unless otherwise defined herein, scientific and technical terminologies employed in the present disclosure shall have the meanings that are commonly understood and used by one of ordinary skill in the art. Also, unless otherwise required by context, it will be understood that singular terms shall include plural forms of the same and plural terms shall include the singular. Specifically, as used herein and in the claims, the singular forms "a" and "an" include the plural reference unless the context clearly indicates otherwise. Also, as used herein and in the claims, the terms "at least one" and "one or more" have the same meaning and include one, two, three, or more.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about". Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques.

As used herein, the term "L-form RNA" (L-RNA) refers to an artificial RNA built from L-ribose. Compared to naturally occurring oligonucleotides (e.g., D-form RNA, D-RNA), which are homochiral and are built from D-ribose, L-RNA is an enantiomeric counterpart of the natural oligonucleotide and is artificially synthesized via chemical reactions by using L-ribose as the major stating material.

As used herein, the term "aptamer" refers to an oligonucleotide (e.g., a DNA or RNA oligonucleotide) having specific binding regions which are capable of forming complexes with an intended target molecule in an environment wherein other substances in the same environment are not complexed to the oligonucleotide.

The term "G-quadruplex structure" (G4 structure) as used herein refers to a four-stranded helical nucleic acid structure comprising multiple stacked G-tetrads, each of which consists of four guanine bases that associate in a cyclical manner through Hoogsteen hydrogen bonds and are further stabilized, through coordination to a cation in the center. The body of stacked G-tetrads, comprising a total of 2-8 layers, is collectively referred to as the G-tetrad core. Each of the four guanine columns constituting the G-tetrad core can arise from a single (continuous column), two, or four (discontinuous column) separate guanine stretch/stretches. The term "parallel G-quadruplex", as used herein, relates to a G-quadruplex structure wherein all four strands point in the same direction.

The term "transcription" is known in the art, and refers to a reaction during which a nucleic acid molecule (e.g., a DNA molecule) serving as a template and having a particular nucleotide sequence is read by an RNA polymerase so that the RNA polymerase produces a single-stranded RNA molecule. During transcription, the genetic information in a nucleic acid template is transcribed, and subsequently the transcribed RNA may be further translated into protein. As used herein, the term "in vitro transcription" refers to a reaction wherein RNA, in particular mRNA, is in vitro synthesized from DNA template in a cell-free system, e.g., appropriate cell extracts. According to some embodiments of the present disclosure, in vitro transcription is carried out by incubating reactants, including DNA template containing a promoter, RNA polymerase, nucleotide triphosphates (NTPs), reaction buffer (e.g., Tris or Tris-HCl), salt (e.g., MgCl$_2$), reducing agent (optionally; e.g., dithiothreitol, DTT) and RNase inhibitor (optionally), at an appropriate temperature (e.g., 37° C.) for a period of time.

As used herein, the term "reverse transcription" refers to a reaction in which an RNA template is reverse transcribed using a reverse transcriptase into a complementary DNA (cDNA) chain. A reverse transcription reaction usually includes. RNA template, reverse transcriptase, reaction buffer (e.g., Tris or Tris-HCl), salt, primers (e.g., oligo (dT) primers or random primers), deoxynucleoside triphosphates (dNTPs), reducing agent (optionally; e.g., dithiothreitol, DTT) and RNase inhibitor (optionally). Depending upon the context, the mixture can be either a complete or incomplete reverse transcription reaction mixture.

II. DESCRIPTION OF THE INVENTION

DNA or RNA aptamers fold into specific secondary and/or tertiary structures to recognize a variety of targeted molecules. As an RNA aptamer composed of unnatural L-RNA nucleotides. L-RNA aptamer (also known as "Spiegelmer") is advantageous in several aspects, including. (1) low immunogenicity: (2) easily synthesized in large quantities in a controlled manner, with defined structure and stoichiometry: (3) resistant to nuclease degradation: (4) highly stable in blood stream and under physical conditions: (5) single-stranded structure that not only allows for a unique tertiary structure and leads to tighter and more specific binding, but also makes L-RNA aptamer smaller in size and easier to enter into cells as compared to DNA aptamers of the same length in nucleotides; and (6) high binding affinity, in which the affinity of L-RNA aptamers to their target molecules (e.g., DNAs, RNAs, peptides or proteins) often lines in the pico- to nano-molar range. Accordingly, L-RNA aptamer may serve as a targeting tool (e.g., G4-targeting tool) in bio-sensing, bio-imaging, diagnostic and/or therapeutic applications.

The present invention therefore is directed to a method of identifying an L-RNA aptamer specific for a target nucleic acid (such as a target DNA or RNA having a G4 structure, i.e., dG4 or rG4) from a DNA library. According to some embodiments of the present disclosure, the DNA library (hereinafter as "DNA N40 library") comprises a plurality of DNAs, each of which has a randomized nucleotide sequence composed of 40 nucleotides in length (N40) (hereinafter as "N40) DNA"). The present method comprises the steps of, (a) producing a plurality of D-RNAs (hereinafter as "N40 D-RNAs") respectively corresponding to the N40 DNAs via in vitro transcription;

(b) mixing the plurality of N40 D-RNAs of step (a) with streptavidin-coated magnetic beads, which are pre-treated with tRNA;

(c) collecting and mixing the supernatant of the product of step (b) with a biotinylated target nucleic acid;

(d) mixing the product of step (c) with streptavidin-coated magnetic beads, which are pre-treated with tRNA;

(e) eluting the precipitate of step (d) with an elution buffer so as to produce a plurality of D-RNAs specific for the target nucleic acid (hereinafter as "target-specific D-RNAs");

(f) producing a plurality of complementary DNAS (cD-NAs) respectively corresponding to the target-specific D-RNAs of step (e) via reverse transcription;

(g) producing a plurality of DNAs respectively corresponding to the plurality of CDNAs of step (f) via PCR;

(h) repeating steps (a) to (g) at least 4 times, in which the in vitro transcription was performed by using the product of step (g), so as to identify a D-RNA aptamer specific for the target nucleic acid; and (i) producing the L-RNA aptamer corresponding to the D-RNA aptamer of step (h).

In the step (a), the DNA N40 library is subjected to in vitro transcription so as to produce N40 D-RNAs. According to some embodiments, the in vitro transcription is carried out by mixing N40 DNAs (serving as DNA templates) with RNA polymerase (e.g., T7, SP6 or T3 RNA polymerase), NTPs (including ATP, UTP, CTP and GTP) and reaction buffer (e.g., T7, SP6 or T3 reaction buffer), followed by incubating at an appropriate temperature (e.g., 37° C.) for a period of time (e.g., 2-3 hours). Optionally, the reaction buffer may contain one or more salts (e.g., MgCl$_2$), reducing agent (e.g., dithiothreitol, DTT), RNase inhibitor or a combination thereof, so as to improve the transcription efficiency. A skilled artisan may adjust the reactants, their concentrations and reaction parameters (e.g., temperature and reaction time) in accordance with intended purposes. The thus-produced N40 D-RNAs respectively have the nucleotide sequences corresponding to the N40 DNAS.

According to some optional embodiments of the present disclosure, the L-RNA aptamer is identified from a single-stranded DNA (ssDNA) library (i.e., ssDNA N40 library). In this case, the method further comprises the step of producing the DNA N40 library from the ssDNA N40) library via reverse transcription prior to step (a). According to one exemplary embodiment, the DNA N40 library is produced by primer extension on the ssDNA of the ssDNA N40 library with reverse primer, in the presence of reverse transcriptase, dNTPs (including dATP, dTTP, dCTP and dGTP) and reaction buffer (e.g., Tris-HCl). Preferably, the reaction buffer contains one or more salts (e.g., MgCl$_2$ and/or LiCl) and/or reducing agent (e.g., DTT) to improve the transcription efficiency.

In the step (b), the N40 D-RNAs of step (a) are subjected to a negative selection via mixing with streptavidin-coated magnetic beads (e.g., streptavidin-coated iron beads). According to preferred embodiments of the present disclosure, the streptavidin-coated magnetic beads are pre-treated with tRNA to inhibit non-specific binding sites.

Optionally, the mixture of the magnetic beads and N40 D-RNAs as described in step (b) is subjected to centrifugation or magnetic field so as to separate beads-bound D-RNAs from non-bound D-RNAs. According to certain embodiments, the mixture of step (b) is centrifuged at low speed (e.g., 100, 200, 300, 400 or 500 rpm) for a period of time (e.g., 1-2 hours) to precipitate the magnetic beads and beads-bound D-RNAs (i.e., D-RNAs which bind to magnetic beads without specificity). According to alternative embodiments, the mixture of step (b) is exposed to a magnetic field to achieve the same purpose.

Then, in the steps (c) and (d), the supernatant of the product of step (b), which contains non-bound D-RNAs, is subjected to a positive selection so as to identify the D-RNAs having binding affinity to the target nucleic acid. In practice, the supernatant of step (b) is collected and then mixed with a biotinylated target nucleic acid, i.e., a target DNA or RNA sequence having a biotin molecule conjugated at its 5'- or 3'-end (step (c)). According to some preferred embodiments, the biotinylated target nucleic acid is a biotinylated L-form RNA (i.e., biotinylated L-rG4). After incubating for a period of time (e.g., 30-60 minutes), the mixture containing non-bound D-RNAs and biotinylated target nucleic acid is further mixed with streptavidin-coated magnetic beads (e.g., streptavidin-coated iron beads), which are pre-treated with tRNA to inhibit non-specific binding sites (step (d)). In this case, the D-RNAs having binding affinity to the target nucleic acid can be isolated from the mixture via the interaction between the complementary sequences of biotinylated target nucleic acid (e.g., biotinylated L-rG4) and the D-RNA, and the streptavidin-biotin interaction between the biotinylated target nucleic acid and streptavidin-coated magnetic beads.

Optionally, the mixture of step (d) is subjected to centrifugation or magnetic field so as to separate beads-bound D-RNAs from non-bound D-RNAs. According to certain embodiments, the mixture of step (d) is centrifuged at low speed (e.g., 100, 200, 300, 400 or 500 rpm) for a period of time (e.g., 1-2 hours) thereby precipitating the magnetic beads and beads-bound D-RNAs (i.e., the D-RNAs bound to magnetic beads via interacting with the biotinylated target nucleic acid). According to alternative embodiments, the mixture of step (d) is exposed to a magnetic field to achieve the same purpose.

In the step (e), the D-RNAs bound to the magnetic beads are eluted with the aid of an elution buffer, which disrupts the binding of the D-RNAs, biotinylated target nucleic acid (e.g., biotinylated L-rG4) and magnetic beads. According to some embodiments of the present disclosure, the elution buffer is an alkaline solution containing a chelating agent, for example, ethylenediaminetetraacetic acid (EDTA).

Next, in the step (f), reverse transcribing the target-specific D-RNAs produced in step (e) into cDNAs (step (f)). The methods and conditions for reverse transcribing an RNA template into its corresponding cDNA are known by the person having ordinary skill in the art; for the sake of brevity, the detailed descriptions are omitted herein. According to some working examples of the present disclosure, the reverse transcription is carried out by mixing the target-specific D-RNAs with reverse transcriptase, reverse primers, dNTPs (including dATP, dTTP, dCTP and dGTP) and reaction buffer (e.g., Tris-HCl), and then incubated at an appropriate temperature (e.g., 50° C.) for a period of time (e.g., 30 minutes). Depending on desired purposes, the reaction buffer may contain one or more salts (e.g., $MgCl_2$ and/or LiCl), reducing agent (e.g., DTT), RNase inhibitor or a combination thereof, thereby improving the transcription efficiency. A skilled artisan may adjust the reactants, their concentrations and reaction parameters (e.g., temperature and reaction time) in accordance with intended purposes. The thus-produced cDNAs respectively have the nucleotide sequences corresponding to the target-specific D-RNAs.

Optionally, the present method further comprises adding an alkaline solution (e.g., NaOH) to the cDNAs of step (f), followed by heating the mixture for a period of time (e.g., heating the mixture at 95° C. for 10 minutes) to degrade RNA and protein. Then, the cDNAs may optionally be neutralized by an acidic solution (e.g., Tris-HCl, pH7.5) and/or purified by a column.

In the step (g), double-stranded DNAs (dsDNAs) corresponding to the cDNAs of step (f) are produced by PCR. The steps and conditions for producing dsDNAs from cDNAs via PCR are known by the person having ordinary skill in the art; for the sake of brevity, the detailed descriptions are omitted herein. According to certain working examples of the present disclosure, the PCR is carried out by mixing the cDNAs of step (f) (serving as templates) with DNA polymerase, forward and reverse primers, dNTPs (including dATP, dTTP, dCTP and dGTP) and reaction buffer (e.g., Tris-HCl). Depending on intended purposes, the reaction buffer may contain one or more salts (e.g., $MgCl_2$).

As described in the step (h), the dsDNAs produced by step (g) may serve as the transcription templates of the next round of selection, i.e., the templates for in vitro transcription of step (a). According to some embodiments, steps (a) to (g) are repeated at least 4 times (e.g., 4, 5, 6, 7, 8, 9, 10 or more times) so as to improve the binding specificity of the selected product (i.e., the target-specific D-RNA and its corresponding cDNA and dsDNA) to the target nucleic acid. According to one exemplary embodiment of the present disclosure, for the purpose of identifying the aptamer L-Apt.12-6, steps (a) to (g) are repeated 4 times. According to another exemplary embodiment of the present disclosure, in the process of identifying the aptamer L-Apt.8f, steps (a) to (g) are repeated 7 times. In these embodiments, the target-specific D-RNA produced by step (e) of the last round of selection exhibits binding affinity and/or specificity towards the target nucleic acid, and is identified as the D-RNA aptamer.

Optionally, the method further comprises subjecting the DNA produced by step (g) of the last round of selection to sequencing technology, for example, next generation sequencing (NGS) or Sanger sequencing, so as to identify the nucleotide sequences of the DNA and its corresponding cDNA and D-RNA aptamer.

Finally, in the step (i), the L-RNA aptamer is chemically synthesized in accordance with the nucleotide sequence of the identified D-RNA aptamer of step (h).

According to some embodiments of the present disclosure, the target nucleic acid is APP RNA that has a G4 structure (i.e., APP rG4) in its 3'-UTR. Preferably, the target nucleic acid is D-form APP RNA (i.e., APP D-rG4, which is present in natural biological systems). In these embodiments, the biotinylated target nucleic acid for positive selection as described in step (c) is a biotinylated L-form APP rG4 (i.e., biotinylated APP L-rG4), and the thus-identified aptamer is referred as "L-Apt.8f".

According to certain embodiments of the present disclosure, the target nucleic acid has a parallel G4 structure, e.g., vascular endothelial growth factor (VEGF) dG4, telomerase RNA component (TERC) dG4, c-myc dG4, B-cell lymphoma-2 (Bel-2) dG4, c-kit dG4, telomeric repeat binding factor 2 (TRF2; also known as "TERF2") rG4, TERC rG4, KRAS proto-oncogene (KRAS) rG4, and Bcl-2 rG4. In these embodiments, the biotinylated target nucleic acid for positive selection as described in step (c) is a biotinylated L-form c-kit rG4 (i.e., biotinylated L-c-kit rG4), and the thus-identified aptamer is referred as "L-Apt.12-6".

Also disclosed herein are two aptamers (i.e., L-Apt.8f and L-Apt.12-6) selected by the present method.

According to some embodiments, the aptamer L-Apt.8f comprises a nucleotide sequence at least 85% (e.g., 85%, 86%, 87%, 88%, 89%, 90%, 91%, 92%, 93%, 94%, 95%, 96%, 97%, 98%, 99% or 100%) identical to SEQ ID NO: 1. Preferably, the aptamer L-Apt.8f comprises a nucleotide sequence 100% identical to SEQ ID NO: 1. According to some working examples, the aptamer L-Apt.8f exhibits binding affinity and specificity towards APP D-rG4, and treatment of aptamer L-Apt.8f regulates APP gene expression in cells.

According to certain embodiments, the aptamer L-Apt.12-6 comprises a nucleotide sequence at least 85% (e.g., 85%, 86%, 87%, 88%, 89%, 90%, 91%, 92%, 93%, 94%, 95%, 96%, 97%, 98%, 99% or 100%) identical to SEQ ID NO: 2. Preferably, the aptamer L-Apt.12-6 comprises a nucleotide sequence 100% identical to SEQ ID NO: 2. According to certain working examples, the aptamer L-Apt.12-6 exhibits binding affinity and specificity towards parallel dG4 and rG4, and the treatment of aptamer L-Apt.12-6 regulates gene activity in cells.

The following Examples are provided to elucidate certain aspects of the present invention and to aid those of skilled in the art in practicing this invention. These Examples are in no way to be considered to limit the scope of the invention in any manner. Without further elaboration, it is believed that one skilled in the art can, based on the description herein, utilize the present invention to its fullest extent. All publications cited herein are hereby incorporated by reference in their entirety.

EXAMPLE

Materials and Methods

In Vitro Selection (rG4-Systematic Evolution of Ligands by Exponential Enrichment, RG4-SELEX)

A single-stranded DNA library (ssDNA N40 library) containing a plurality of ssDNA was synthesized, wherein each of the ssDNA had a randomized nucleotide sequence composed of 40 nucleotides in length (N40). The dsDNA library (DNA N40 library) was obtained by primer extension on 2 μM ssDNA library with 300 nM reverse primers, 10 U/μL reverse transcriptase and 1 mM dNTP mixture in 20 μL reaction buffer containing 20 mM Tris-HCl (pH 7.5), 4 mM MgCl$_2$, 1 mM DTT and 150 mM LiCl. The generated dsDNA products were purified by DNA column and used for in vitro transcription reaction. Transcription reaction was performed with RNA synthesis kit in a 40 μL reaction. After incubating at 37° C. for 2.5 hours, 2 U DNase was added and incubated at 37° C. for another 15 minutes. The synthesized RNA library was purified by 10% denaturing polyacrylamide gel electrophoresis (PAGE) and subsequent RNA column purification.

For the purpose of selection, MyOne™ Streptavidin C1 dynabeads (3 mg) were washed and blocked with 0.1 mg/mL yeast tRNA by shaking at 300 rpm, 25° C. for 1 hour. Specific amount of RNA library in selection buffer containing 150 mM KCl, 1 or 5 mM MgCl$_2$ and 25 mM Tris-HCl was heated at 75° C. for 3 minutes and cooled down at room temperature for 10 minutes. Then, 1 mg tRNA-blocked dynabeads was added to RNA library for negative selection. The mixture was incubated at 300 rpm, 25° C. for 1 or 2 hours. Beads were discarded to remove beads-bound RNAs. Supernatant was collected for positive selection with certain concentration of biotinylated target nucleic acid (i.e., biotinylated L-c-kit or L-APP rG4 respectively comprised the nucleotide sequence of SEQ ID NOs: 3 and 4). The mixture was incubated at 25° C. or 37° C. for 30 or 60 minutes. Then, 2 mg tRNA-blocked dynabeads was added and shaked at 25° C. for 30 minutes. The supernatant was discarded after beads separation. Beads were washed 5 times using 600 μL selection buffer before elution with 25 mM NaOH and 1 mM EDTA. The obtained RNA solution was neutralized by 5 μL of 1 M Tris-HCl (pH 7.5), followed by RNA column purification. The purified RNAs were reverse transcribed to cDNA with 300 nM reverse primer, 10 U/μL reverse transcriptase and 1 mM dNTP mixture in 60 μL reaction buffer containing 20 mM Tris-HCl (pH 7.5), 4 mM MgCl$_2$, 1 mM DTT and 150 mM LiCl. After incubating at 50° C. for 30 minutes, 3 μL of 2 M NaOH was added and heated at 95° C.

for 10 minutes to degrade RNA and protein. The obtained DNA solution was neutralized by 15 μL of 1 M Tris-HCl (pH 7.5) followed by column purification. Then, PCR was carried out using cDNA, DNA polymerase master mix, 500 nM forward and reverse primers in a 40 μL reaction. After dsDNA column purification, the dsDNA library was used for in vitro transcription for the next selection round.

For the purpose of identifying an L-RNA aptamer specific for c-kit, four rounds of selection were performed in total, and their corresponding conditions including RNA library input, MgCl$_2$ concentration, negative selection time, L-c-kit input, positive selection time and temperature, beads washing time and PCR cycles were summarized in Table 1.

TABLE 1

| Conditions used for the in vitro selection process. | | | | |
|---|---|---|---|---|
| Selection rounds | 1 | 2 | 3 | 4 |
| MgCl$_2$ concentration (mM) | 5 | 5 | 5 | 1 |
| D-RNA library (μM) | 3 | 1 | 0.3 | 0.1 |
| Biotin-L-c-kit (μM) | 0.65 | 0.65 | 0.33 | 0.1 |
| Negative selection time (h) | 2 | 2 | 2 | 1 |
| Positive selection time (min) | 30 | 30 | 30 | 30 |
| Washing time (min) | 1 | 1 | 1 | 10 |
| Incubation temperature (° C.) | 25 | 25 | 37 | 37 |
| PCR cycles | 8 | 8 | 8 | 8 |

After 4 rounds of selection, the final selected DNA was amplified by PCR to add barcode and linker sequences for NGS purpose. After confirming the nucleotide sequence of the DNA and its corresponding D-RNA, the L-RNA aptamer "L-Apt.12-6" was chemically synthesized to recognize c-kit D-dG4 target.

For the purpose of identifying an L-RNA aptamer specific for APP, 7 rounds of selection were performed in total. The final selected DNA was ligated into TOPO vector by TA cloning and sequenced by Sanger sequencing. After confirming the nucleotide sequence of the DNA and its corresponding D-RNA, L-RNA aptamer "L-Apt.8f" was chemically synthesized to recognize APP D-rG4 target.

Figure 1B:
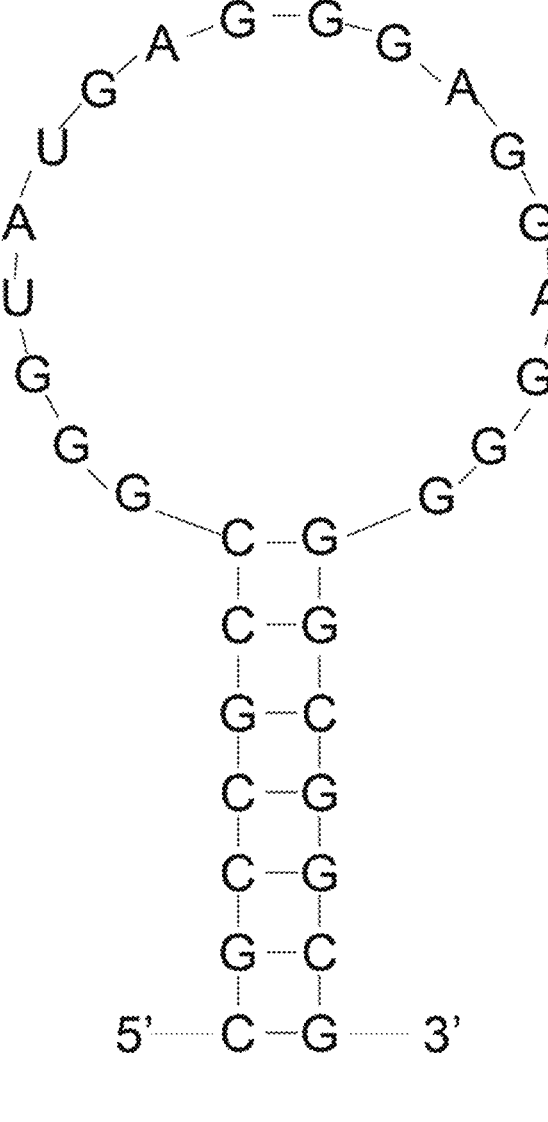

The nucleotide sequences of L-Apt.8f and L-Apt.12-6 were summarized in Table 2. According to computational prediction, both L-Apt.8f and L-Apt.12-6 are predicted to possess a G4 structure (FIGS. 1A and 1B).

TABLE 2

| Nucleotide sequences of L-Apt. 8f and L-Apt. 12-6 | | |
|---|---|---|
| Aptamer | Nucleotide sequence | SEQ ID NO |
| L-Apt. 8f | GCGGCAAGAGUGUGGGAGG GGGGUCGACGCCGC | 1 |
| L-Apt. 12-6 | CGCCGCCGGGUAUGAGGGA GGAGGGGGCGGCG | 2 |

Electrophoretic Mobility Shift Assay (EMSA)

A total 20 μL sample mixtures were prepared which consisted of 10 nM 5'-FAM labeled target nucleic acid (i.e., APP L- or D-rG4, or c-kit L-dG4), 1 mM MgCl$_2$, 25 mM Tris-HCl (pH 8.0), 150 mM KCl and 8% of sucrose solution with a vary of concentration of the aptamer. The sample solution was then denatured for 5 minutes at 95° C. and incubated at 37° C. for 30 minutes. 18 μL of samples were loaded to a 10% (19:1, acrylamide:bis-acrylamide) native non-denaturing polyacrylamide gel in 150 mM potassium acetate, 1 mM $MgCl_2$ and 25 mM Tris-HCl (pH 8.0) at 4° C. The electrophoresis was conducted at 70 mA for 120 minutes in a 4° C. fridge. Gel imager was used to scan the gel under 650 V. The image obtained was then quantified and analyzed with software. One site-specific binding model from software was employed for the determination of curve fitting and $K_d$ value.

Circular Dichroism (CD) Spectroscopy

CD spectrophotometer was employed for the CD spectroscopy. A reaction mixture with total of 2 mL was transferred to a quartz cuvette with 1-cm path length. The sample solutions containing of 5 µM D-aptamer, 10 mM LiCac (pH 7.0) and 150 mM KCl or LiCl were thoroughly mixed and heated to denature the solutions for 5 minutes under 95° C. The solutions were then cooled and renatured for 15 minutes under room temperature. The reaction mixtures were all scanned under 25° C. with the range from 220 to 310 nm and the spectra in every 1 nm. There was 0.5 s/nm responding time and all of the spectra recorded were averaged with 2 times of scanning. The data obtained was then normalized for the finding of the molar residue ellipticity and then smoothed over 5 $nm^3$. Software was used to undergo all analysis with the collected data.

Thermal Melting Monitored by UV Spectroscopy

An ultraviolet-visible (UV-Vis) spectrophotometer was used for performing UV-melting spectroscopy. The sample solutions were made with the same conditions exactly as stated in the CD spectroscopy experiment. All data were measured with a rate of temperature increment of 0.5° C./min and heated with a range of temperature 5-95° C. and the transitions of aptamer was observed at 295 nm. The whole set of data were smoothed over 11 nm and further studied through software.

Ligand Enhanced Fluorescence Assay

Sample solutions with a total of 100 µL containing 1 µM D-aptamer (D-Apt.8f or D-Apt.12-6), 150 mM LiCl or KCl solution, 10 mM LiCac buffer (pH 7.0) and finally 1 µM Thioflavin T (ThT) or N-methyl mesophorphyrin IX (NMM) ligand. The fluorescence assay was measured with the used of fluorometer. First, the samples were prepared without the presence of ligand and heated for 5 minutes at 95° C. for denaturation then renatured under room temperature for 15 minutes. The sample solutions were then transferred into a quartz cuvette with 1-cm path length and excited at 394 nm for NMM ligand and 425 nm for ThT ligand. The range from 550 to 750 nm of emission spectra were used for NMM while for ThT, the range of emission spectra is from 440 to 700 nm. All data were scanned under 25° C. every 2 nm and 5 nm for both the entrance and exit slit widths. All of data was analyzed through software.

EMSA for Binding Specificity

Sample mixtures consisted of 10 or 20 nM 5'-FAM labeled target, 1 mM $MgCl_2$, 8% of sucrose solution, 25 mM Tris-HCl (pH 8.0) and 150 mM KCl while 100 nM of L-aptamer (L-Apt.8f or L-Apt.12-6) was added in positive samples were denatured by heating under 95° C. for 5 minutes and renatured under 37° C. for 30 minutes. 18 µL of samples were loaded to a 10% (19:1, acrylamide:bis-acrylamide) native non-denaturing polyacrylamide gel in 150 mM potassium acetate, 25 mM Tris-HCl (pH 8.0) and 1 mM $MgCl_2$ at 4° C. The electrophoresis was conducted at 70 mA for 90-120 minutes in a 4° C. fridge. Imaging system and gel imager were used to scan the gel under 650 V. The image obtained was then quantified and analyzed with software.

Microscale Thermophoresis (MST)

16 sets of 10 µL containing 25 mM Tris-HCl (pH 8.0), 150 mM KCl, 40 nM of 5'-FAM labeled APP L- or D-rG4, a vary concentration of $MgCl_2$ and L- or D-aptamer with increasing concentration were made and heated for 5 minutes at 95° C. and then cooled to 4° C. for 5 minutes. The sample solution was then incubated for 30 minutes at 37° C. Sample solution was loaded to the capillary tubes which were especially made for MST measurement and scanned at room temperature with the mode of blue light from the MST binding software. All readings collected were analyzed for the $K_d$ value by software.

Cell Imaging

Cells were seeded on 3.5 cm confocal dish one day before transfection. Next day, FAM-L-aptamer was heated to 95° C. for 3 minutes and annealed at room temperature and cells were transfected with FAM-L-aptamer using Lipofectamine™ 2000. After 22 hours post transfection, cells were stained with 5 µg/ml Hoechst 33342 for 15 minutes at 37° C. Then cells were scanned by laser confocal scanning microscope.

Dual Luciferase Reporter Gene Assay

For the purpose of evaluating the effect of the present aptamers on gene expression in cells, a dual luciferase reporter vector was used in the study. In structure, the dual luciferase reporter vector contained, from 5'-end to 3'-end, in sequence, a simian virus 40 (SV40) promoter, a *Renilla* luciferase gene operably linked to the SV40 promoter, a herpes simplex virus-thymidine kinase (HSV-TK) promoter, and a Firefly luciferase gene operably linked to the HSV-TK promoter.

Figure 2A:
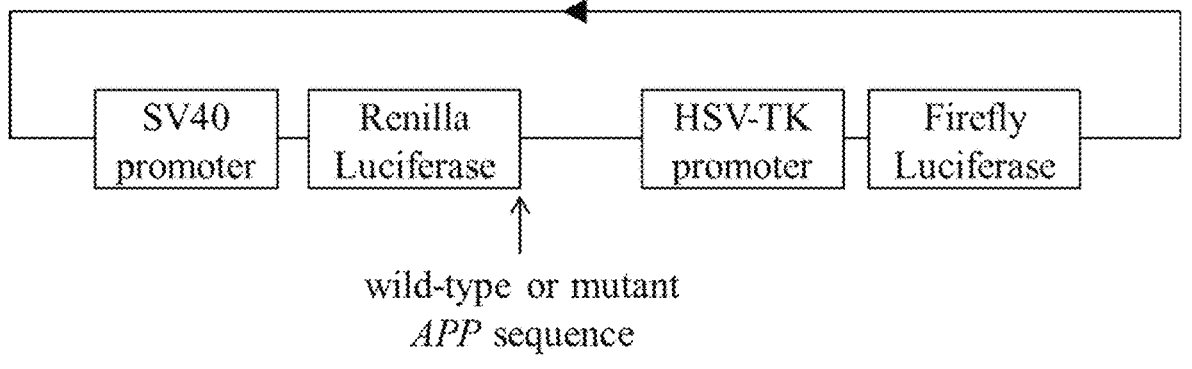
FIGS. 2A and 2B are schematic diagrams respectively depicting the design of dual luciferase reporter plasmids according to another embodiment of the present disclosure.

To determine the effect of L-Apt.8f on gene expression, the sequence containing APP wild-type G4 (wt) or APP mutant G4 (mut) motif was inserted into the 3'-UTR of the *Renilla* luciferase gene (FIG. 2A). The thus-constructed plasmids were respectively referred as "WT APP plasmid" and "mutant APP plasmid". Then, the constructed reporter plasmid was transfected into HeLa cells in the presence or absence of L-Apt.8f aptamer. D-Apt.8f, which does not bind to APP D-rG4, was used as a negative control in this cellular experiment.

Figure 2B:
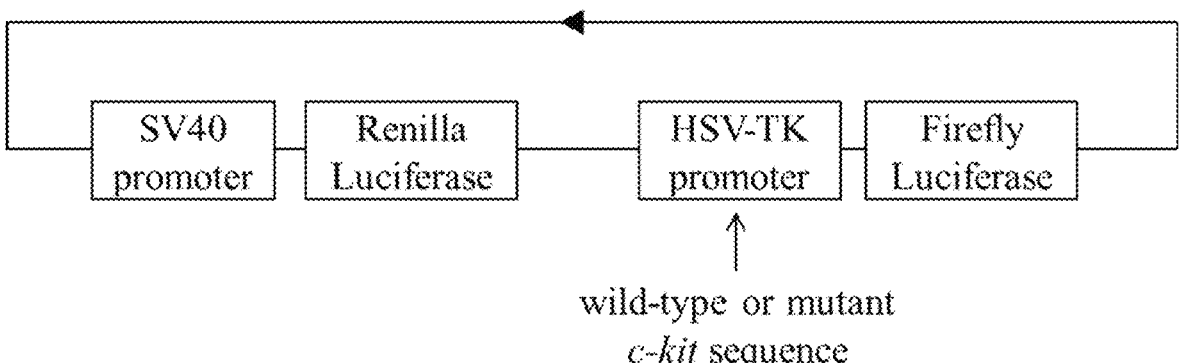

To determine the effect of L-Apt.12-6 on gene expression, wild-type and mutant c-kit sequences were respectively inserted into the HSV-TK promoter at SacII restriction enzyme site of the dual luciferase reporter vector (FIG. 2B). The thus-constructed plasmids were respectively referred as "WT c-kit plasmid" and "mutant c-kit plasmid". Then, the constructed reporter plasmid was transfected into HeLa cells in the presence or absence of L-Apt.12-6 aptamer.

22 hours post-transfection. Firefly and *Renilla* luciferase activities were determined according to the manufacturer's manual using the dual luciferase reporter assay system. In all cases. *Renilla* luciferase values were normalized as control by Firefly luciferase.

Example 1 Characterization of Aptamer L-Apt.8f 1.1 Identification and Optimization of D-RNA Aptamers Using rG4-SELEX and APP L-rG4 Target To generate an aptamer specific for APP D-rG4, the chirality of the intended target APP D-rG4 was reversed, in which a biotin group was added to the 5'-end to produce biotin-APP L-rG4. rG4-SELEX with a N40 D-RNA random library pool was employed in this study. Through an iterative process, non-binding D-RNA aptamers were discarded and D-RNA aptamers binding to the APP L-rG4 target were enriched in each rG4-SELEX round. A negative selection was adopted by incubating the D-RNA pool with tRNA-blocked streptavidin beads to remove non-APP L-rG4 specific binders (bead-specific binders), and the remaining D-RNA pool was incubated with biotin-APP L-rG4 (positive selection). After washing, elution, and reverse transcription, PCR, and transcription, the transcribed RNA pool was subjected to next round selection. After 7 rounds of selection, enriched D-RNA aptamer candidates were cloned and sequenced.

From the Sanger sequencing results, two D-RNA aptamer candidates referred as D-Apt.8 and D-Apt.21 were selected for testing, and their Mfold predicted secondary structures were analyzed. To verify whether the two candidates could interact with APP L-rG4, the aptamers were transcribed and purified, and initial binding test with FAM-APP L-rG4 target using electrophoretic mobility shift assay (EMSA) was performed. The EMSA result indicated that APP L-rG4 could bind with D-Apt.8 and D-Apt.21 strongly, with dissociation constants (Kas) being $11.14 \pm 1.43$ nM and $67.54 \pm 11.27$ nM, respectively (data not shown). As D-Apt.8 exhibited a stronger binding affinity than D-Apt.21. D-Apt.8 was therefore used as the candidate for downstream study. D-Apt.8 is a 39 nucleotide (nt) long aptamer, which contains 3 stems and 3 loops (data not shown). In order to minimize the length of D-Apt.8 candidate, 2 truncated versions were designed by splitting D-Apt.8 according to its predicted secondary structure, which were respectively referred as D-Apt.8e and D-Apt.8f. The binding affinity of D-Apt.8e and D-Apt.8f to APP L-rG4 was then examined separately, and the data indicated that only D-Apt.8f recognized APP L-rG4 strongly with a $K_d$ value of $49.23 \pm 4.89$ nM (data not shown), while D-Apt.8e exhibited no observable binding (data not shown). The binding was also verified with microscale thermophoresis (MST) assay, and the analytic results demonstrated consistent binding profile between APP L-rG4 with D-Apt.8f, with a $K_d$ value of $62.92 \pm 16.29$ nM (data not shown). Based on these results. D-Apt.8f, a 33 nt long aptamer, was chosen as the aptamer candidate for further characterization.

1.2 Biophysical Characterization of D-RNA Aptamer D-Apt.8f

Computational G4 prediction was first performed using G4RNA screener, and the result indicated that D-Apt.8 and D-Apt.8f, but not D-Apt.8e, exhibited cGcC, G4H, and G4NN scores that exceeded the default threshold set for G4 formation in these programs (data not shown), an indication that D-Apt.8f might contain an rG4 motif. To experimentally validate this proposition, 4 different spectroscopy assays were employed to characterize D-Apt.8. First, circular dichroism (CD) detection was performed under 150 mM $K^+$- or $Li^+$-containing conditions, and the results indicated that the CD signal was dependent on monovalent cation ($K^+$ versus $Li^+$) (data not shown), supporting rG4 formation. Moreover, the CD spectrum displayed a positive peak at 264 nm and a negative peak at 240 nm under $K^+$ condition (data not shown), suggestive of rG4 in parallel topology. Second, UV-melting monitored was conducted at 295 nm under 150 mM $K^+$, and the result indicated a hypochromic shift profile (data not shown), which is a hallmark for rG4 formation. The melting temperature (Tm) was determined to be 70.5° C. suggesting the rG4 motif is thermostable under physiological temperature. Last, G4-specific ligands including NMM and ThT were used to carry out G4 ligand fluorescence enhancement assays, and Apt.8f was detected with NMM and ThT fluorescence enhancement by an approximately 3.6 and 1.8 folds, respectively, when comparing 150 mM K versus 150 mM Li conditions (data not shown). Taken together, these data all supported the formation of thermostable, parallel rG4 motif in Apt.8f.

1.3 Mutagenesis Analysis of D-RNA Aptamer D-Apt.8f

To investigate the effect of the sequence and structure of D-Apt.8f towards APP L-rG4 recognition, a number of mutagenesis constructs were designed, tested, and analyzed by EMSA. First, whether the sequence and/or base pair structure is critical in stem 1 was tested by designing a base pair co-variation mutant Apt.8f-19 (M19), and no change in binding affinity was found as compared to Apt.8f (WT) (data not shown), supporting that the base pair structure, but not sequence of stem 1 was critical for the recognition. Second, whether the sequence and/or structure is crucial in stem 2 was evaluated by designing 2 base pair strengthening mutants (M3 and M8) that changed $G_{14}G_{26}$ mismatch to $G_{14}C_{26}$ or $C_{14}G_{26}$ base pair, respectively. We found no observable binding for both of these constructs (data not shown), highlighting that stem 2 base pair strengthening was bad for the target recognition. Based on the biophysical characterization results above (data not shown), it was expected that some of the Gs in D-Apt.8f would involve in the formation of rG4 motif, which was not predictable by Mfold program. Third, to explore which of the Gs plays a key role in the binding, single nucleotide mutation was systematically performed to replace each Gs in the loop 1, stem 2, and loop 2 to As, and the EMSA result indicated that except mutation in $G_8$ (M1) that had no effect, all other mutations either caused complete disruption including $G_{15}$ (M11), or partial disruption including $G_{10}$ (M2), $G_{12}$ (M10), $G_{16}$ (M16), $G_{18}$ (M6), $G_{19}$ (M12), $G_{20}$ (M13), $G_{21}$ (M14), $G_{22}$ (M15), $G_{23}$ (M7) in binding (data not shown). Finally, as loop 2 contained a G-run of 6 Gs, and the single mutant in loop 2 only caused partial disruption in binding, a few double mutants in the loop 2 were also assessed and the data indicated that the Gs in the middle. $G_{19}$-$G_{20}$ (M4), $G_{20}$-$G_{21}$ (M17), $G_{21}$-$G_{22}$ (M5), were more sensitive in target recognition as compared to the one on/near the sides, $G_{18}$ and $G_{23}$ (M9) and $G_{19}$ and $G_{22}$ (M18) (data not shown). From these mutagenesis experiments, nucleotides in the D-Apt.8f that are critical for the binding to APP L-rG4 were identified.

1.4 Binding Affinity and Metal Ion-Dependence of L-RNA Aptamer—D-Target Interaction The enantiomeric specificity of Apt.8f was tested in this example, and the results indicated that D-Apt.8f only interacted with APP L-rG4 but not APP D-rG4 (data not shown). Similarly, L-Apt.8f interacted strongly with APP D-rG4, and only very weakly with APP L-rG4 (data not shown). These findings supported that the Apt.8f and APP rG4 interaction is enantiomeric-specific and depends on the chirality of the aptamer and target. To determine the $K_d$ of the L-Apt.8f with APP D-rG4. EMSA was performed and the data indicated that L-Apt.8f interacted with APP D-rG4 strongly, with a $K_d$ value of $24.06 \pm 2.90$ nM (data not shown), which was similar to the EMSA results of D-Apt.8f-APP L-rG4 mentioned above.

As the L-aptamer—D-target interaction relies on tertiary interaction and non-Watson Crick base pairing, it is hypothesized that magnesium ion may have a key role in the L-Apt.8f-APP D-rG4 complex formation. To test this idea. MST under three different magnesium ion concentration (0 mM, 1 mM, 5 mM) was performed, and the results indicated that the binding affinity lowered with increasing magnesium ion level, indicating the supporting role of magnesium ion in mediating the interaction (data not shown). To assess the role of rG4 motif in the complex formation. MST experiments were also carried out by replacing the potassium ion (G4 stabilizing ion) to lithium ion (G4 non-stabilizing ion), and a dramatic loss of binding, with $K_d$ value of larger than 3 μM (data not shown), was observed, highlighting the essential role of potassium ion and rG4 motif in the interaction.

1.5 Binding Specificity of L-RNA Aptamer to Intended Target and Non-Targets

To investigate whether the binding of L-Ap8f was specific to APP D-rG4, altogether 17 other constructs were tested with EMSA (data not shown). Non-G4 motifs such as hairpins (DNA hairpin and RNA hairpin), as well as single-stranded homopolynucleotides (poly rA, poly rU and poly rC), were first tested, and the data indicated that the tested non-G4 did not bind to L-Apt.8f (data not shown), suggesting the binding was G4-specific. Similarly, no binding was detected when different dG4s (hTELO, Bel2Mid, c-Kit and c-Myc) were used (data not shown), highlighting that L-Apt.8f also do not bind to dG4s tested. Given that rG4s and dG4s both contain G-quartets, this interesting result suggest other structural features may have a critical role in recognition. To go one step further, several other rG4s (Kras1, MT3, TRF2, Bel2, hTERC, TERRA and NRAS) were designed, and their binding to L-Apt.8f was examined: the overall results demonstrated that most of them (5 out of 7), except Kras1 rG4 and Bel2 rG4, did not bind to L-Apt.8f (data not shown), indicating good specificity of L-Apt.8f. In addition, the APP rG4 mutant motif (Mut APP rG4) where the middle Gs were mutated to As was tested, and the results indicated much weaker binding affinity than APP rG4 (data not shown). Overall, these results demonstrated that L-Apt.8f binds preferentially to APP rG4 over non-G4 and dG4 constructs, and it showed promising performance in distinguishing APP rG4 over other closely related rG4s, as well as the APP rG4 mutant.

1.6 Application of L-Apt.8f to Regulate APP Gene Expression in Cells

Figure 3A:
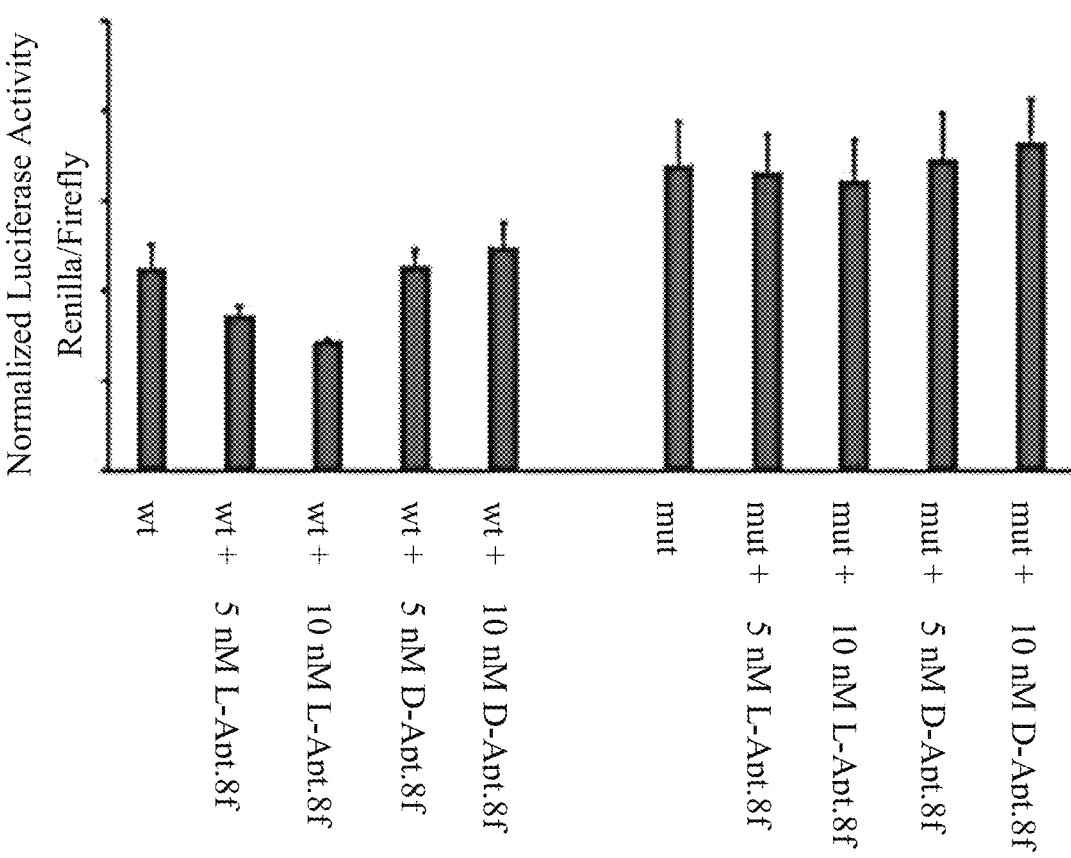
FIG. 3A is a histogram depicting the effect of aptamer L-Apt.8f on gene expression in cells according to Example 1 of the present disclosure.

To demonstrate the utility of L-Apt.8f, the effect of L-Apt.8f treatment on gene expression in cells was examined using dual luciferase gene reporter assay. As described in Materials and Methods, the plasmid containing APP wild-type G4 or APP mutant G4 sequence (i.e., WT APP plasmid or mutant APP plasmid) was transfected into cells in the presence or absence of L-Apt.8f aptamer. To verify whether L-Apt.8f can get inside cells, confocal microscopy was conducted, and the data suggested FAM-labeled L-Apt.8f can be transfected successfully into Hela cells (data not shown). From the reporter gene assay result, it is found that the WT APP plasmid had less luciferase activity than the mutant APP plasmid in the absence of any treatment (data not shown). Importantly, it is also observed that L-Apt.8f treatment can further suppress the expression of the relative luciferase activity of the WT APP plasmid in a concentration-dependent manner, and the L-Apt.8f treatment had no effect on the expression of the relative luciferase of mutant APP plasmid (FIG. 3A), indicating the regulation is G4-dependent. D-Apt.8f serving as the control group had no effect on both WT APP plasmid and mutant APP plasmid (FIG. 3A), suggested that L-Apt.8f specifically binds to APP 3'-UTR rG4 to regulate gene expression in cells. To address whether L-Apt.8f influenced the transcription or translation of reporter gene, the relative mRNA population of luciferase was tested by quantitative reverse transcription PCR (RT-qPCR) and no difference was observed in the mRNA level (data not shown), indicating that the suppressive role of L-Apt.8f on APP 3'-UTR rG4 was at the translational level but not in transcriptional level. Together. L-Apt.8f can negatively control gene expression through interacting with APP rG4 structure.

Example 2 Characterization of Aptamer L-Apt.12-6

The EMSA data demonstrated the binding between Apt.12-6 and FAM-L-c-kit, in which with increasing concentration of Apt.12-6 (0, 5, 10, 25, 50, 100, 200, 500, 1000 or 2000 nM), the unbound band intensity decreased and the bound band intensity increased, indicating the interaction between Apt12-6 and FAM-L-c-kit (data not shown). According to the results, Apt.12-6 recognized FAM-L-c-kit 1 strongly, with a $K_d$ value of 40.9±1.7 nM (data not shown).

G4-specific ligands including NMM and ThT were used to carry out G4 ligand fluorescence enhancement assays, and the K'-dependent enhanced fluorescence in NMM and ThT supported the formation of rG4 in Apt.12-6 (data not shown). CD spectrum further confirmed the formation of a parallel G4 structure in Apt.12-6 (data not shown).

According to the results of EMSA. L-Apt.12-6 recognized FAM-D-c-kit, in which with increasing concentration of L-Apt.12-6 (0, 5, 10, 25, 50, 100, 200, 500, 1000 or 2000 nM), the unbound band intensity decreased and the bound band intensity increased, indicating the interaction between L-Apt.12-6 and FAM-D-c-kit. The $K_d$ determined by the biding curve of FAM-D-c-kit against L-Apt.12-6 was 42.3±1.9 nM (data not shown). The binding of L-Apt.12-6 and different G4 targets, including parallel dG4 (such as VEGF dG4. TERC dG4, c-myc dG4, Bel-2 dG4 and c-kit dG4), antiparallel dG4 (such as TBA dG4 and hras-1 dG4), hybrid dG4 (such as SYNDIG1 dG4, 2GKU dG4, AKT1 dG4 and hTelo dG4) and parallel rG4 (such as TRF2 rG4, hTERC rG4, KRAS rG4 and Bel-2 rG4), was determined, and the results suggested that L-Apt.12-6 can specifically bind to parallel G4 target (including parallel dG4 target and parallel rG4 target), but not antiparallel or hybrid G4. These data demonstrated that L-Apt.12-6 recognize specifically to G4s with parallel topology.

In the DNA polymerase stop assay, primer extension of DNA templates containing G4 generate full length and stop products, and aptamer/ligand binding to G4 can further inhibit primer extension and generate more stop products. According to the results of denaturing PAGE for the DNA polymerase stop assay in the presence of wild-type or mutant parallel dG4 c-kit. L-Apt.12-6 can inhibit the full length product of wild-type c-kit template, but not for mutant c-kit template, wild-type or mutant hras-1 and hTelo templates. These results suggested that L-Apt.12-6 can interact with parallel dG4s to induce DNA polymerase stop.

Figure 3B:
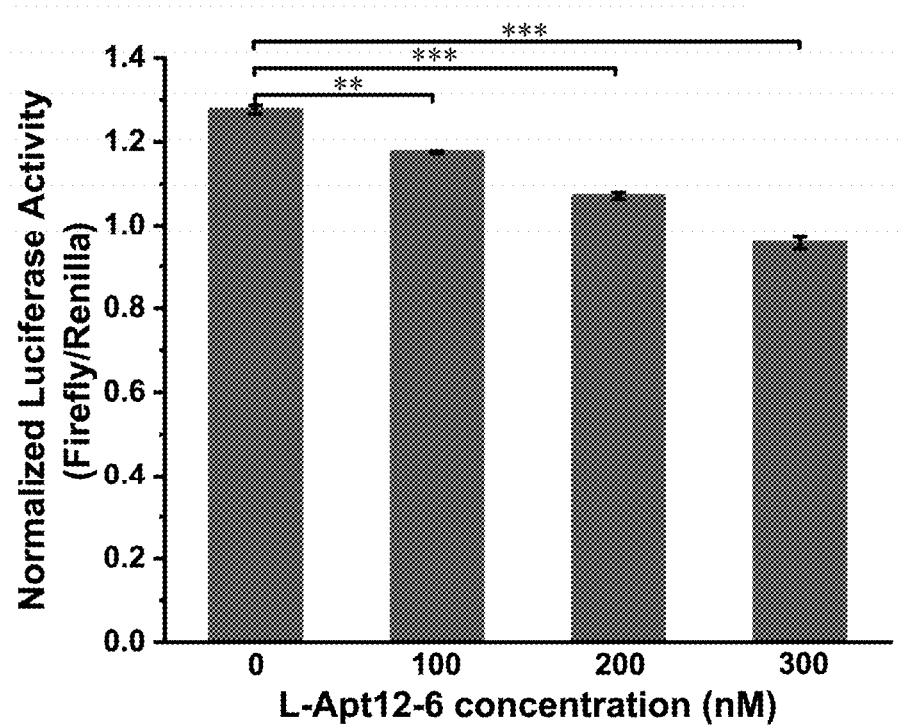
FIG. 3B depicts the effect of aptamer L-Apt.12-6 on gene expression in cells according to Example 2 of the present disclosure: Panel (A): Normalized luciferase activity of cells transfected with wild-type c-kit plasmid and L-Apt.12-6; Panel (B): Normalized luciferase activity of cells transfected with mutant c-kit plasmid and L-Apt.12-6; Panel (C): Relative luciferase mRNA expression levels of cells transfected with wild-type c-kit plasmid and L-Apt.12-6; Panel (D): Relative luciferase mRNA expression levels of cells transfected with mutant c-kit plasmid and L-Apt.12-6; the error bar represents the standard deviation of four independent replicates; *, $p<0.05$; , $p<0.01$; *, $p<0.001$; ns: not significant.
Figure 3B:
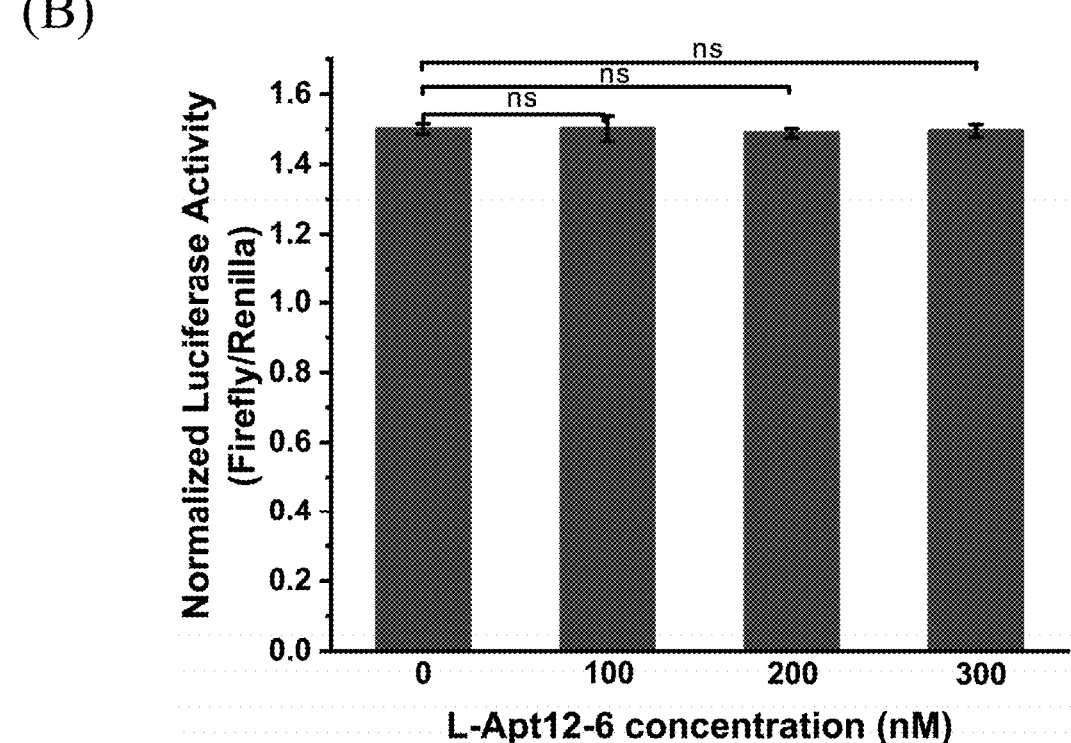
Figure 3B:
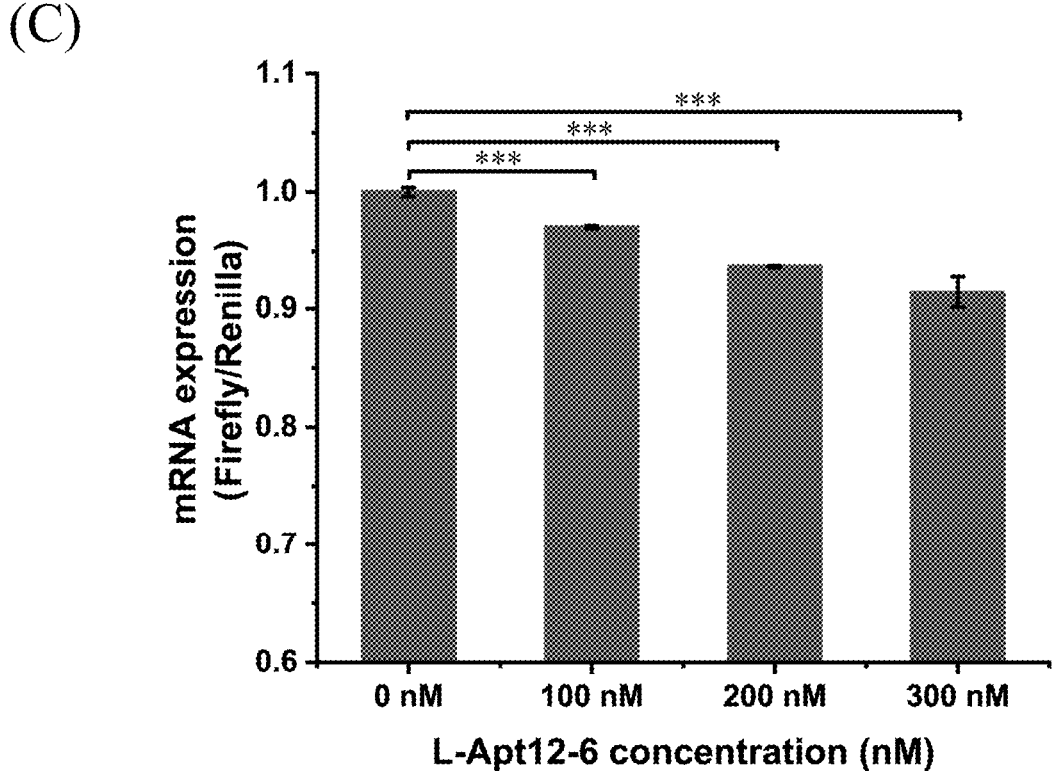
Figure 3B:
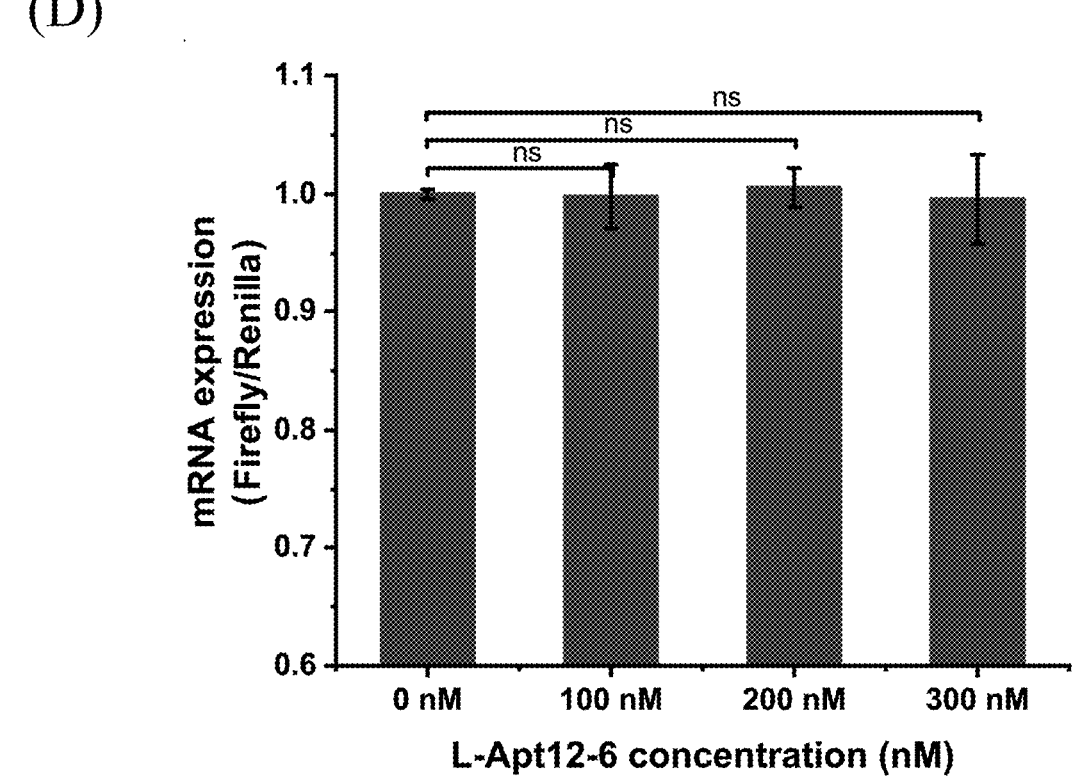

As described in Materials and Methods, the plasmid containing wild-type (WT) or mutant c-kit sequence (i.e., WT c-kit plasmid or mutant e-kit plasmid) was transfected into cells in the presence or absence of L-Apt.12-6 aptamer. *Renilla* luciferase was used as internal control to account for transfection variation. With increasing L-Apt.12-6 (0, 100 nM, 200 nM or 300 nM) treatment in cells, the luciferase activity level of the WT e-kit plasmid decreased (Panel (A) of FIG. 3B), while no significant change was observed in the cells transfected with the mutant c-kit plasmid (Panel (B) of FIG. 3B). Similarly, the treatment of L-Apt.12-6 decreased the mRNA expression level of the WT c-kit plasmid in a dose-dependent manner (Panel (C) of FIG. 3B), while no significant change was observed in the cells transfected with the mutant c-kit plasmid (Panel (D) of FIG. 3B). The results demonstrated that L-Apt.12-6 can regulate reporter gene activity in cells.

It will be understood that the above description of embodiments is given by way of example only and that various modifications may be made by those with ordinary skill in the art. The above specification provides a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. An L-form ribonucleic acid (L-RNA) aptamer specific for the 3'-untranslated region (3'-UTR) of amyloid precursor protein (APP) messenger RNA (mRNA), comprising the nucleotide sequence of SEQ ID NO: 1.

2. An L-form ribonucleic acid (L-RNA) aptamer specific for a target nucleic acid having a parallel G-quadruplex structure, comprising the nucleotide sequence of SEQ ID NO: 2.

3. The L-RNA aptamer of claim 2, wherein the target nucleic acid is the promoter of c-kit gene.

*     *     *     *     *

SEQUENCE LISTING

```
Sequence total quantity: 4
SEQ ID NO: 1               moltype = RNA   length = 33
FEATURE                    Location/Qualifiers
source                     1..33
                           mol_type = other RNA
                           organism = synthetic construct
SEQUENCE: 1
gcggcaagag tgtgggaggg gggtcgacgc cgc                                    33

SEQ ID NO: 2               moltype = RNA   length = 32
FEATURE                    Location/Qualifiers
source                     1..32
                           mol_type = other RNA
                           organism = synthetic construct
SEQUENCE: 2
cgccgccggg tatgagggag gaggggcgg cg                                      32

SEQ ID NO: 3               moltype = DNA   length = 22
FEATURE                    Location/Qualifiers
source                     1..22
                           mol_type = other DNA
                           organism = synthetic construct
SEQUENCE: 3
agggagggcg ctgggaggag gg                                                22

SEQ ID NO: 4               moltype = RNA   length = 18
FEATURE                    Location/Qualifiers
source                     1..18
                           mol_type = other RNA
                           organism = synthetic construct
SEQUENCE: 4
ggggcgggtg gggagggg                                                     18
```